United States Patent
Lee et al.

(10) Patent No.: US 11,123,301 B2
(45) Date of Patent: *Sep. 21, 2021

(54) CERIA NANOCOMPOSITE COMPRISING CERIA NANOPARTICLE FOR TREATING SUBARACHNOID HEMORRHAGE, METHOD FOR PREPARING SAME, AND PHARMACEUTICAL COMPOSITION

(71) Applicants: Cenyx Biotech Inc., Seoul (KR); Seoul National University Hospital, Seoul (KR); Research & Business Foundation Sungkyunkwan University, Suwon-si (KR)

(72) Inventors: Seung-Hoon Lee, Seoul (KR); Han-Gil Jeong, Seoul (KR); Do Yeon Kim, Seoul (KR); Dong-Wan Kang, Seoul (KR); Jaeyun Kim, Suwon-si (KR); Bong Geun Cha, Seoul (KR)

(73) Assignee: Cenyx Biotech Inc., Seoul (KR)

( * ) Notice: Subject to any disclaimer, the term of this patent is extended or adjusted under 35 U.S.C. 154(b) by 80 days.

This patent is subject to a terminal disclaimer.

(21) Appl. No.: 16/343,378

(22) PCT Filed: Oct. 21, 2016

(86) PCT No.: PCT/KR2016/011937
§ 371 (c)(1),
(2) Date: Apr. 18, 2019

(87) PCT Pub. No.: WO2018/074641
PCT Pub. Date: Apr. 26, 2018

(65) Prior Publication Data
US 2019/0240161 A1 Aug. 8, 2019

(30) Foreign Application Priority Data
Oct. 21, 2016 (KR) ........................ 10-2016-0137505

(51) Int. Cl.
| A61K 9/51 | (2006.01) |
| A61K 9/50 | (2006.01) |
| A61K 33/00 | (2006.01) |
| A61P 9/00 | (2006.01) |
| A61P 25/00 | (2006.01) |
| A61K 9/00 | (2006.01) |

(52) U.S. Cl.
CPC .......... *A61K 9/5031* (2013.01); *A61K 9/0019* (2013.01); *A61K 9/5146* (2013.01); *A61K 9/5192* (2013.01); *A61K 33/00* (2013.01); *A61P 9/00* (2018.01); *A61P 25/00* (2018.01)

(58) Field of Classification Search
None
See application file for complete search history.

(56) References Cited

U.S. PATENT DOCUMENTS

| 2007/0123996 A1 | 5/2007 | Sugaya et al. |
| 2012/0070500 A1 | 3/2012 | Cimini et al. |
| 2014/0271899 A1 | 9/2014 | Leiter et al. |
| 2015/0079162 A1 | 3/2015 | Hyeon et al. |
| 2015/0315561 A1 | 11/2015 | Schabbauer et al. |
| 2019/0381187 A1 | 12/2019 | Lee et al. |

FOREIGN PATENT DOCUMENTS

| KR | 10-2006-0056895 | 5/2006 |
| KR | 10-2013-0114469 | 10/2013 |

OTHER PUBLICATIONS

Nguyen et al., "A general procedure to synthesize highly crystalline metal oxide and mixed oxidenanocrystals in aqueous medium and photocatalytic activity of metal/oxide nanohybrids," Nanoscale 3(4):1861-1873, 2011.
International Search Report and Written Opinion for PCT/KR2016/011937, dated Jul. 10, 2017.
Kang, Dong-Wan. "Anti-inflammatory Effects of Ceria Nanoparticles in Experimental Intracerebral Hemorrhage Models," The 7th Japanese-Korean Joint Stroke Conference, Scientific Symposium 2 (Oct. 24, 2015).
Kim, Chi Kyung et al., "Anti-inflammatory Effects of Ceria Nanoparticles in Experimental Intracerebral Hemorrhage Models," Stroke, 47(Suppl 1), Abstract No. A WP265 (Feb. 2016).
Kim, Chi Kyung et al., "Ceria Nanoparticles that Can Protect against Ischemic Stroke," Angewandte Chemie International Edition, 51(44):11039-11043 (Sep. 2012).
Kim, Tae Ho et al., "Mesoporous Silica-coated Luminescent $Eu^{3+}$ Doped $GdVO_4$ Nanoparticles for Multimodal Imaging and Drug Delivery," RSC Advances, 4(86):45687-45695 (Sep. 2014).
Notice of Allowance for Korean Patent Application No. 10-2016-0137505 (dated Sep. 4, 2018) (with machine translation).
Office Action for Korean Patent Application No. 10-2016-0137505 (dated Jan. 1, 2018) (with machine translation).
Office Action for Korean Patent Application No. 10-2016-0137505 (dated Jul. 16, 2018) (with machine translation).
Yu, Tae Kyung et al., "Aqueous-phase Synthesis of Single-crystal Ceria Nanosheets," Angewandte Chemie International Edition, 49(26):4484-4487 (Jun. 2010).
Pirmohamed, Talib et al., "Nanoceria exhibit redox state-dependent catalase mimetic activity," Chemical Communication, 46(16):2736-2738 (Mar. 2010).
Restriction Requirement for U.S. Appl. No. 16/474,049, dated May 5, 2020.

(Continued)

Primary Examiner — Jennifer A Berrios
(74) Attorney, Agent, or Firm — Klarquist Sparkman, LLP (57) ABSTRACT

Provided are a ceria nanocomposite including a ceria nanoparticle for treating subarachnoid hemorrhage, a method of preparing the same, and a pharmaceutical composition including the ceria nanocomposite. The ceria nanocomposite for treating subarachnoid hemorrhage disclosed herein includes a ceria nanoparticle and a surface modified layer disposed on a surface of the ceria nanoparticle, wherein the surface modified layer includes a polyethylene glycol residue.

6 Claims, 6 Drawing Sheets

(56) References Cited

OTHER PUBLICATIONS

Garcia et al., "Neurological deficit and extent of neuronal necrosis attributable to middle cerebral artery occlusion in rats: statistical validation," *Stroke*, 26(4):627-634 (Apr. 1995).
Sugawara et al., "A new grading system evaluating bleeding scale in filament perforation subarachnoid hemorrhage rat model," *J Neurosci Methods*, 167(2):327-334 (Jan. 2008).
Methods in Molecular Biology, vol. 203: In Situ Detection of DNA Damage: Methods and Protocols, Edited by: V. V. Didenko © Humana Press Inc., Totowa, NJ (2002).
International Search Report and Written Opinion for PCT/KR2017/000353, dated Sep. 12, 2017 (w/English translation of International Search Report).
Korsvik, Cassandra et al., "Superoxide Dismutase Mimetic Properties Exhibited by Vacancy Engineered Ceria Nanoparticles," *Chemical Communication*, 10(10).1056-1058 (Mar. 2007).

CERIA NANOCOMPOSITE COMPRISING CERIA NANOPARTICLE FOR TREATING SUBARACHNOID HEMORRHAGE, METHOD FOR PREPARING SAME, AND PHARMACEUTICAL COMPOSITION

CROSS REFERENCE TO RELATED APPLICATIONS

This is the U.S. National Stage of International Application No. PCT/KR2016/011937, filed Oct. 21, 2016, which in turn claims the benefit of Korean Patent Application No. 10-2016-0137505, filed Oct. 21, 2016, which application is incorporated herein in its entirety.

TECHNICAL FIELD

The present disclosure relates to a ceria nanocomposite including a ceria nanoparticle for treating subarachnoid hemorrhage, a method of preparing the same, and a pharmaceutical composition including the ceria nanocomposite, and more particularly, to a ceria nanocomposite including a ceria nanoparticle and a surface modified layer for treating subarachnoid hemorrhage, a method of preparing the same, and a pharmaceutical composition including the ceria nanocomposite.

BACKGROUND ART

Subarachnoid hemorrhage (SAH) refers to a subtype of intracranial hemorrhage, and is a disease that causes various inflammatory reactions and brain cell damage in the brain tissue located at the periphery of the brain parenchyma by blood extravasated from intracranial blood vessels to the subarachnoid space.

Since SAH is a hemorrhage that occurs in the subarachnoid space, a space surrounding the brain tissue, it causes damage throughout the whole brain, leading to mortality or severe permanent brain damage. The causes of SAH include brain trauma and a rupture of intracranial aneurysm, bulge or distention of an artery wall. In terms of prognosis, SAH is a disease with a high mortality and poor prognosis in spite of the development of modern medicine. Among the patients with SAH, 10~15% of the patients die even before arrival at a hospital, and 25% of the patients die within 24 hours after the hemorrhage onset. Moreover, even if surviving patients arrive at the hospital, an average of 40% of the patients die within a month, and 50% of the patients die within 6 months. Overall, 51~80% of the SAH patients eventually die. Even if the patients survive, rebleeding, hydrocephalus, and vasospasm that occur within 2 weeks cause further neurological deterioration, and most of the patients have poor cognitive function and are unable to live their daily lives due to permanent brain damage. Such patients are bed-ridden for the rest of their lives, or may not be able to walk due to the motor weakness.

Although SAH is a dangerous disease as described above, and is known to have a poor prognosis, no treatment for acute brain damage caused by extravasated blood is currently available. The currently available care is only focused on prevention and care of neurological complications—obliteration of intracranial aneurysms to prevent rebleeding, managing intracranial pressure via ventriculo-peritoneal shunt when hydrocephalus occur, etc.

Regarding the acute brain damage caused by SAH, blood components such as hemoglobin and thrombin cause inflammatory cascades, leading to brain edema, and brain tissue necrosis. In this inflammatory response, oxidative stress caused by reactive oxygen is an important cause of brain tissue necrosis. In this regard, doctors and scientists have made an effort to prevent brain damage caused by SAH, but no satisfactory treatment has yet been developed.

DESCRIPTION OF EMBODIMENTS

Technical Problem

Provided is a ceria nanocomposite including a ceria nanoparticle for treating subarachnoid hemorrhage.

Provided is a method of preparing the ceria nanocomposite for treating subarachnoid hemorrhage.

Provided is a pharmaceutical composition including the ceria nanocomposite for treating subarachnoid hemorrhage.

Solution to Problem

According to an aspect of the present disclosure, there is provided a ceria nanocomposite for treating subarachnoid hemorrhage including:

a ceria nanoparticle and a surface modified layer disposed on a surface of the ceria nanoparticle, wherein the surface modified layer includes a polyethylene glycol (PEG) residue.

The surface modified layer may include an outer layer including the PEG residue and an inner layer whose one end is combined with the ceria nanoparticle and the other end is combined with the PEG residue.

The inner layer may include a residue of a polyfunctional organic compound including a first terminal group capable of binding to the ceria nanoparticle and a second terminal group capable of binding to a PEG derivative which is an origin of the polyethylene glycol residue.

The polyfunctional organic compound may include an aliphatic aminocarboxylic acid.

The PEG derivative may include methoxy PEG succinimidyl glutarate, methoxy PEG succinimidyl barate, methoxy PEG succinimidyl carbonate, methoxy PEG succinimidyl succinate, methoxy PEG succinimidyl propionate, or a combination thereof.

The ceria nanocomposite may have an average particle diameter of about 5 nm to about 100 nm.

According to another aspect of the present disclosure, there is provided a method of preparing a ceria nanocomposite for treating subarachnoid hemorrhage, the method including:

preparing a mixed solution containing a cerium precursor, a polyfunctional dispersion stabilizer, and a first solvent;

heating the mixed solution to prepare a ceria nanoparticle in which the polyfunctional dispersion stabilizer is attached to a surface of the ceria nanoparticle; and mixing the ceria nanoparticle with a polyethylene glycol derivative in a second solvent such that the polyfunctional dispersion stabilizer and the polyethylene glycol derivative are combined together and a ceria nanocomposite is thereby prepared.

According to another aspect of the present disclosure, there is provided a pharmaceutical composition including the ceria nanocomposite for treating subarachnoid hemorrhage.

Advantageous Effects of Disclosure

A ceria nanocomposite for treating subarachnoid hemorrhage according to an embodiment of the present disclosure reduces a mortality rate and neurological damage resulting from subarachnoid hemorrhage, and also exhibits excellent antioxidant and anti-inflammatory effects. Thus, the ceria nanocomposite can be useful for treating subarachnoid hemorrhage.

BEST MODE

Hereinafter, a ceria nanocomposite for treating subarachnoid hemorrhage according to an embodiment of the present invention will be described in detail.

According to an aspect of the present disclosure, a ceria nanocomposite for treating subarachnoid hemorrhage may include a ceria ($CeO_2$) nanoparticle and a surface modified layer disposed on a surface of the ceria nanoparticle.

In detail, the surface modified layer may be disposed to at least partially surround a surface of the ceria nanoparticle. For example, the surface modified layer may be composed of a plurality of materials that are radially disposed at predetermined intervals on the surface of the ceria nanoparticle.

The ceria nanoparticle has excellent antioxidative and anti-inflammatory effects, and reduce a mortality rate and neurological damage that are caused by subarachnoid hemorrhage.

The surface modified layer may improve biocompatibility and biosafety of the ceria nanocomposite including the same.

In addition, the surface modified layer may prevent the ceria nanocomposite from being uptaken by a phagocyte or the like by increasing the overall size of the ceria nanocomposite.

In addition, the surface modified layer has a hydrophilic surface so that, when the ceria nanocomposite is injected into the blood, the ceria nanocomposite allows it to adhere first to water molecules in the blood, and prevent it from adhering to other ions in the blood. Accordingly, the aggregation between the ceria nanocomposites may be prevented, and the colloidal stability of the ceria nanocomposite may be enhanced.

The surface modified layer may include a polyethylene glycol (PEG) residue.

The origin of the polyethylene glycol residue may be a polyethylene glycol derivative. The term "polyethylene glycol derivative" as used herein refers to a material formed by substituting at least one of two terminal hydrogens of polyethylene glycol with other substituents (for example, an alkoxy group, an succinimidyl ester group, or the like).

The polyethylene glycol derivative may have a weight average molecular weight of about 100 daltons (Da) to about 10,000 Da depending on the number of ethylene oxide(s) in a polymer chain.

The polyethylene glycol derivative may include methoxy polyethylene glycol (PEG) succinimidyl glutarate, methoxy PEG succinimidyl barate, methoxy PEG succinimidyl carbonate, methoxy PEG succinimidyl succinate, methoxy PEG succinimidyl propionate, or a combination thereof, but embodiments of the present disclosure are not limited thereto. For use as the polyethylene glycol derivative, a variety of compounds capable of binding to a polyfunctional organic compound may be used.

In addition, the surface modified layer may include an outer layer and an inner layer that are combined together.

The outer layer may include the polyethylene glycol residue.

One end of the inner layer is capable of binding to the ceria nanoparticle, and the other end of the inner layer is capable of binding to the polyethylene glycol residue. For example, one end of the inner layer is capable of chemically binding (e.g., covalently bonding) to the ceria nanoparticle, and the other end of the inner layer is also capable of chemically binding (e.g., covalently bonding) to the polyethylene glycol residue.

The inner layer may include a residue of a polyfunctional organic compound including a first terminal group (e.g., a carboxylic group) that is capable of binding to the ceria nanoparticle and a second terminal group (e.g., an amine group) that is capable of binding to the polyethylene glycol derivative which is the origin of the polyethylene glycol residue. The term "polyfunctional organic compound" as used herein refers to an organic compound having two or more functional groups.

The polyfunctional organic compound may include an aliphatic aminocarboxylic acid.

The aliphatic aminocarboxylic acid may include 6-aminohexanoic acid, 5-aminopentanoic acid, 4-aminobutanoic acid, aminocaproic acid, aminoundecanoic acid, aminolauric acid, or a combination thereof.

The ceria nanocomposite may have an average particle diameter in a range of about 5 nm to about 100 nm, for example, about 5 nm to about 50 nm. When the ceria nanocomposite has the average particle diameter within the range above, the ceria nanocomposite may exhibit excellent water dispersibility and biocompatibility.

Figure 1:
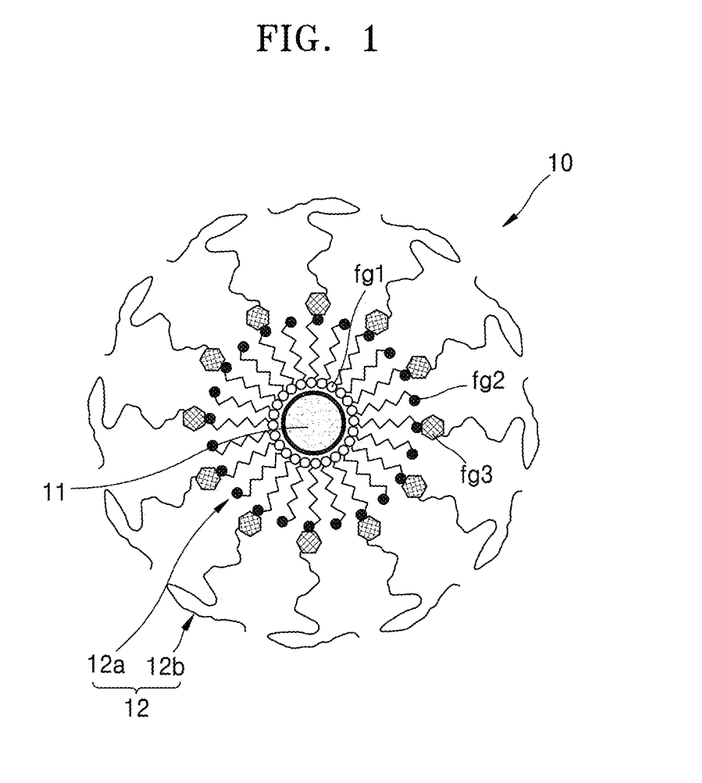
FIG. 1 is a schematic diagram of a ceria nanocomposite according to an embodiment.

FIG. 1 is a schematic diagram of a ceria nanocomposite 10 according to an embodiment of the present disclosure.

Referring to FIG. 1, the ceria nanocomposite 10 includes a ceria nanoparticle 11 and a surface modified layer 12 disposed on the ceria nanoparticle 11.

The surface modified layer 12 includes an inner layer 12a and an outer layer 12b that are connected to each other.

The inner layer 12a includes a polyfunctional organic compound residue having a first terminal residue fg1 combined with the ceria nanoparticle 11 and a second terminal residue fg2 combined with the outer layer 12b.

The outer layer 12b includes a polyethylene glycol derivative residue having a third terminal residue fg3 combined with the second terminal residue fg2 of the polyfunctional organic compound residue included in the inner layer 12a.

According to another aspect of the present disclosure, a pharmaceutical composition may include the ceria nanocomposite for treating subarachnoid hemorrhage.

The pharmaceutical composition may further include a pharmaceutically acceptable additive, and the additive may be, for example, a pH adjusting agent, an isotonization agent, a preservative, other excipients, or a combination thereof.

The pH adjusting agent may include sodium hydroxide, potassium hydroxide, sodium bicarbonate, ammonia liquor, potassium citrate, triethanolamine, sodium citrate, or a combination thereof.

The isotonization agent may include D-mannitol, sorbitol, or a combination thereof.

The preservative may include methyl paraoxybenzoate, ethyl paraoxybenzoate, sorbic acid, phenol, cresol, chlorocresol, or a combination thereof.

An administration route of the ceria nanocomposite for treating subarachnoid hemorrhage or the pharmaceutical composition including the same may include intravenous administration, intraarterial administration, intraperitoneal administration, oral administration, intramedullary administration, inhalation administration, intranasal administration, subcutaneous administration, intracranial administration, intraventricular administration, intrathecal administration, epidural administration, or the like.

A daily dosage of the ceria nanocomposite or the pharmaceutical composition including the same may be variously adjusted depending on a patient's age, symptom, dosage form, or the like. For example, a daily dosage of the ceria nanocomposite of the pharmaceutical composition including the same may be in a range of about 0.5 mg/kg to about 5 mg/kg, for example, about 1 mg/kg to about 2 mg/kg.

The ceria nanocomposite or the pharmaceutical composition including the same may efficiently reach the cytoplasm through the cell membrane to induce reduction of the brain water content and reduction of a cell death rate in a subarachnoid hemorrhage region and a surrounding region of hemorrhage. Accordingly, the ceria nanocomposite or the pharmaceutical composition including the same may exhibit excellent effects, such as antioxidation, anti-inflammation, and the like, thereby improving the survival rate and the functional recovery in surviving individuals.

Hereinafter, a method of preparing the ceria nanocomposite for treating subarachnoid hemorrhage will be described in detail.

The method of preparing the ceria nanocomposite includes: a step of preparing a mixed solution containing a cerium precursor, a polyfunctional dispersion stabilizer, and a first solvent (S10): a step of heating the mixed solution to prepare a ceria nanoparticle in which the polyfunctional dispersion stabilizer is attached to a surface of the ceria nanoparticle (S20); and a step of mixing the ceria nanoparticle with a polyethylene glycol derivative in a second solvent such that the polyfunctional dispersion stabilizer and the polyethylene glycol derivative are combined together and a ceria nanocomposite is thereby prepared (S30).

The step S30 may be referred to as pegylation of the ceria nanoparticle.

The cerium precursor may include cerium(III) acetate hydrate, cerium(III) acetylacetonate hydrate, cerium(III) carbonate hydrate, cerium(IV) hydroxide, cerium(III) fluoride, cerium(IV) fluoride, cerium(III) chloride, cerium(III) chloride heptahydrate, cerium(III) bromide, cerium(III) iodide, cerium(III) nitrate hexahydrate, cerium(III) oxalate hydrate, cerium(III) sulfate, cerium(III) sulfate hydrate, cerium(IV) sulfate, or a combination thereof.

The polyfunctional dispersion stabilizer may be the same as the polyfunctional organic compound described above.

The heating of the mixed solution may be performed at a temperature of about 80° C. to about 95° C. for about 0.5 minutes to about 1 hour.

The step S10 and the step S20 may each be performed as follows: a cerium precursor solution containing a cerium precursor and a first solvent is prepared, and a dispersion stabilizer solution containing a polyfunctional dispersion stabilizer and a first solvent is prepared. Then, the dispersion stabilizer solution is heated to a temperature of about 80° C. to about 95° C. and the cerium precursor solution is added to the heated dispersion stabilizer solution. The resulting solution was left for about 1 minute to about 1 hour.

The polyethylene glycol derivative may be the same as the polyethylene glycol derivative described above.

The first solvent and the second solvent may each be an aqueous solvent. When the first solvent and the second solvent are each an aqueous solvent, the prepared ceria nanocomposite may have little or no toxicity. Thus, when the prepared ceria nanocomposite is injected into the human body, the occurrence of side effects can be minimized.

The aqueous solvent may include water, alcohol (e.g., ethanol, methanol, propanol, or the like), or a combination thereof.

Hereinafter, the present invention will be described with reference to the following examples, but the present invention is not limited thereto.

EXAMPLES

Example 1: Preparation of Ceria Nanocomposite (Preparation of Ceria Nanoparticles)
6-aminohexanoic acid (1.3117 g, Sigma-Aldrich, St. Louis, Mo.) was dissolved in deionized water (60 mL), and the mixed solution was heated to a temperature of 95° C. in the air while being stirred, thereby preparing a first solution. Then, 37 weight % of HCl (70 μl, Duksan Pure Chemicals, South Korea) was added to the first solution to adjust pH of the first solution to 5.5. Meanwhile, cerium(III) nitrate hexahydrate ($Ce(NO_3)_3 \cdot 6H_2O$, 1.08557 g, Alfa Aeser, Ward Hill, Mass.) was dissolved in deionized water (50 mL) at room temperature (about 20° C.), thereby preparing a second solution. Afterwards, the second solution was added to the first solution, thereby preparing a third solution. The temperature of the third solution was maintained at a temperature of 95° C. for 1 minute, and then, cooled to room temperature (about 20° C.). As a result, ceria nanoparticles including 6-aminohexanoic acid combined with surfaces of the ceria nanoparticles were obtained. Afterwards, the ceria nanoparticles were washed three times with acetone to remove unreacted materials.

(Pegylation of the Ceria Nanoparticle)
20 mg of the prepared ceria nanoparticles was added to 2 mL of deionized water, thereby preparing a suspension. The suspension was mixed with 500 mg of a solution in which methoxy polyethylene glycol succinimidyl glutarate (weight average molecular weight: 5,000 Da) was dissolved in 40 mL of ethanol. The mixed solution was stirred at room temperature for 12 hours so that the amine group of 6-aminohexanoic acid combined with the surface of the ceria nanoparticle was covalently bonded to the succinimidyl group of methoxy polyethylene glycol succinimidyl glutarate, thereby eventually obtaining a ceria nanocomposite.

EVALUATION EXAMPLES

Evaluation Example 1: Effect of Ceria Nanocomposite on Improvement of Survival Rates in Terms of Therapeutic Effect on Subarachnoid Hemorrhage (SAH)

To evaluate effect of the ceria nanocomposite prepared according to Example 1 on the improvement of survival rates, a sparague-dawley (SD) rat (KOATECH Co., Ltd.) was anesthetized with isoflurane. Then, a puncture was made on the left middle cerebral artery by using a 4-0 prolene needle, so as to induce SAH. After 6 hours and 30 hours from the induction of SAH, the SD rat was injected with 0.5 mg/kg of the ceria nanocomposite twice in total, or as a control group, the SD rat was injected with the same volume of phosphate buffered saline (PBS) (Amresco Company, pH 7.1 to 7.3) twice in total. From the time of the induction of SAH to the $21^{st}$ day after the induction, it was periodically confirmed whether or not the SD rats were dead, and the survival rate results are shown in FIG. 2.

Figure 2:
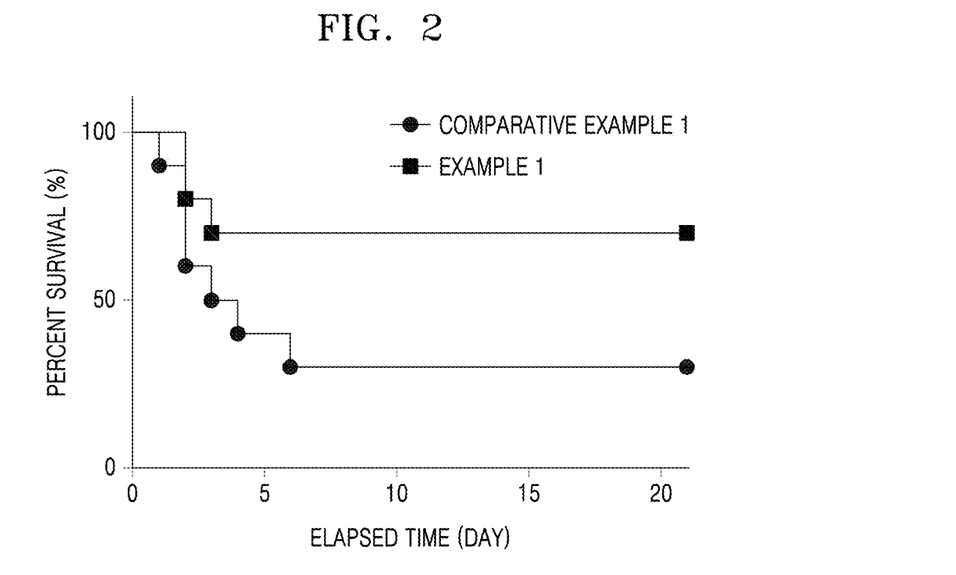
FIG. 2 is a graph showing survival rates to indicate a therapeutic effect of a ceria nanocomposite and phosphate buffered saline (PBS) on subarachnoid hemorrhage.

Referring to FIG. 2, it was confirmed that a mortality rate of the SD rat injected with the ceria nanocomposite according to Example 1 was lower than that of the control group (that is, the SD rat injected with PBS) of Comparative Example 1. In detail, the mortality rate of the control group was 70%, whereas the mortality rate in the case where the ceria nanocomposite was injected was 30%. In Example 1 and Comparative Example 1, 10 SD rats were respectively tested, and the average value was indicated as a survival rate.

Figure 3:
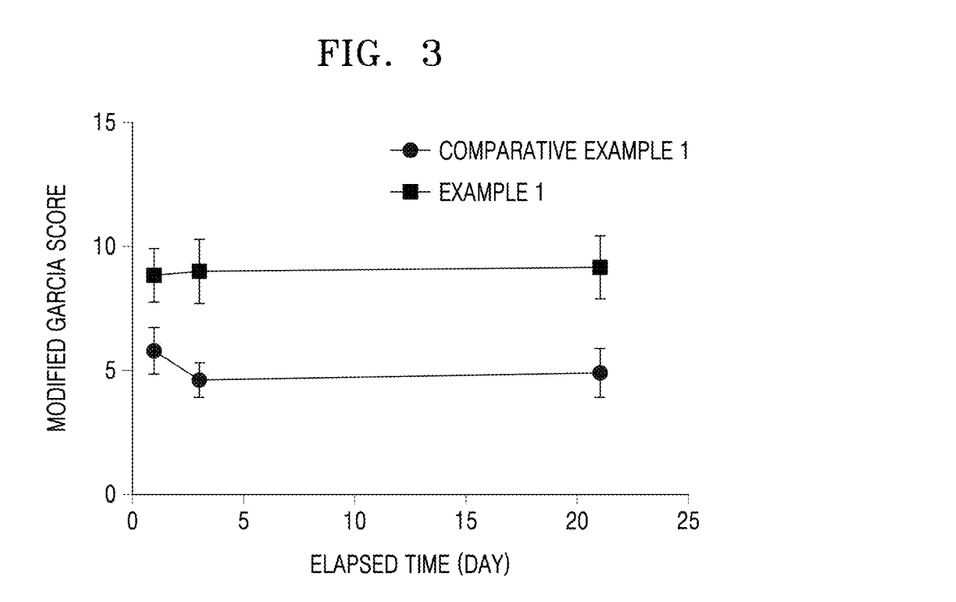
FIG. 3 is a graph showing an extent of neurological damage to indicate a therapeutic effect of a ceria nanocomposite and PBS on subarachnoid hemorrhage.

Evaluation Example 2: Effect of Ceria Nanocomposite on Reduction of Neurological Damage in Terms of Therapeutic Effect on SAH To evaluate effect of the ceria nanocomposite prepared according to Example 1 on the reduction of neurological damage, an SD rat (KOATECH Co., Ltd.) was anesthetized with isoflurane. Then, a puncture was made on the left middle cerebral artery by using a 4-0 prolene needle, so as to induce SAH. After 6 hours and 30 hours from the induction of SAH, the SD rat was injected with 0.5 mg/kg of the ceria nanocomposite twice in total, or as a control group, the SD rat was injected with the same volume of PBS (Amresco Company, pH 7.1 to 7.3) twice in total. From the time of the induction of SAH to the $21^{st}$ day after the induction, the behavior scores of the SD rats were periodically assessed based on the modified Garcia score system, and the results are shown in FIG. 3. The modified Garcia score system is described in detail in the following two research papers.

Garcia J H, Wagner S, Liu K F, Hu X J (1995) Neurological deficit and extent of neuronal necrosis attributable to middle cerebral artery occlusion in rats: statistical validation. Stroke 26:627-634

Sugawara T, Ayer R, Jadhav V, Zhang J H (2008) A new grading system evaluating hemorrhage scale in filament perforation subarachnoid hemorrhage rat model. Neurosci Methods 167:327-334

Referring to FIG. 3, it was confirmed that the SD rat injected with the ceria nanocomposite according to Example 1 left less neurological damage compared to the control group (that is, the SD rat injected with PBS), and accordingly, neurological deficits were relatively decreased. In Example 1 and Comparative Example 1, 10 SD rats were respectively tested, and the average value was indicated as a modified Garcia score.

Evaluation Example 3: Effect of Ceria Nanocomposite on Reduction of Total Brain Water Contents in Both the Left Hemisphere and the Right Hemisphere in Terms of Therapeutic Effect on SAH To evaluate anti-inflammatory effect of the ceria nanocomposite prepared according to Example 1, the brain water contents of the SD rat (KOATECH Co., Ltd.) without SAH (sham model, Reference Example 1), the SD rat into which PBS (Amresco Company, pH 7.1 to 7.3) was injected twice in total, i.e., after 6 hours and 30 hours from the cause of SAH (Comparative Example 1), and the SD rat into which the ceria nanocomposite was injected twice in total, i.e., after 6 hours and 30 hours from the cause of SAH (Example 1) were evaluated according to the conditions shown in Table 1 below. The sham model was prepared in a way that a subcutaneous layer of an SD rat was only peeled off to expose the carotid artery in the neck of the SD rat and then the neck was sutured.

TABLE 1

|  | Reference Example 1 | Comparative Example 1 | Example 1 |
| --- | --- | --- | --- |
| Injection amount of PBS | — | Volume corresponding to injection amount of ceria nanocomposite of Example 1 | — |
| Injection amount of ceria nanocomposite (mg/kg) | — | — | 0.5 |
| Point of brain extraction | 72 hours after preparation of sham model | 72 hours after occurrence of SAH | 72 hours after occurrence of SAH |

After the brain was extracted from each of the SD rats, the brain stem and the cerebellum were removed, and the left hemisphere and the right hemisphere were separated. Afterwards, the wet weight of the left hemisphere and the wet weight of the right hemisphere were respectively measured. Then, the left hemisphere and the right hemisphere were dried at a temperature of 100° C. for 24 hours, and the dry weight of each brain was measured. According to Equation 1 below, the brain water content was calculated.

$$\text{Brain water content in (\%)} = (\text{Wet weight} - \text{dry weight})/\text{wet weight} \times 100 \qquad [\text{Equation 1}]$$

Figure 4:
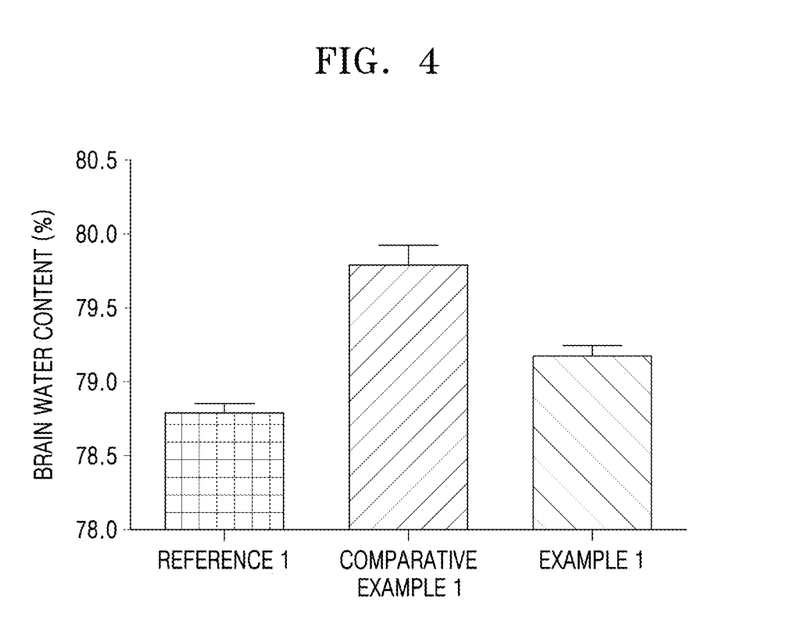
FIG. 4 is a graph showing total brain water content of the cerebral hemispheres to indicate a therapeutic effect of a ceria nanocomposite and PBS on subarachnoid hemorrhage.

The total brain water content in both the left hemisphere and the right hemisphere, i.e., the sum of the brain water content in the left hemisphere and the water content in the right hemisphere, were shown in FIG. 4.

Referring to FIG. 4, it was confirmed that the SD rat injected with the ceria nanocomposite according to Example 1 showed a decrease in the total brain water content compared to the control group (that is, the SD rat injected with PBS) of Comparative Example 1. Here, the smaller the brain water content, the less the edema in hemorrhage regions, meaning excellent anti-inflammatory effect.

Figure 5:
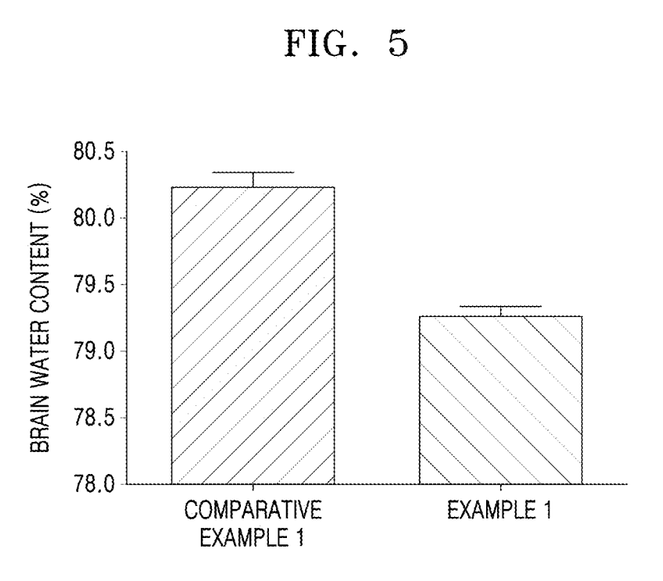
FIGS. 5 and 6 are graphs each showing brain water contents of the left hemisphere and the right hemisphere, respectively, to indicate a therapeutic effect of a ceria nanocomposite and PBS on subarachnoid hemorrhage.
Figure 6:
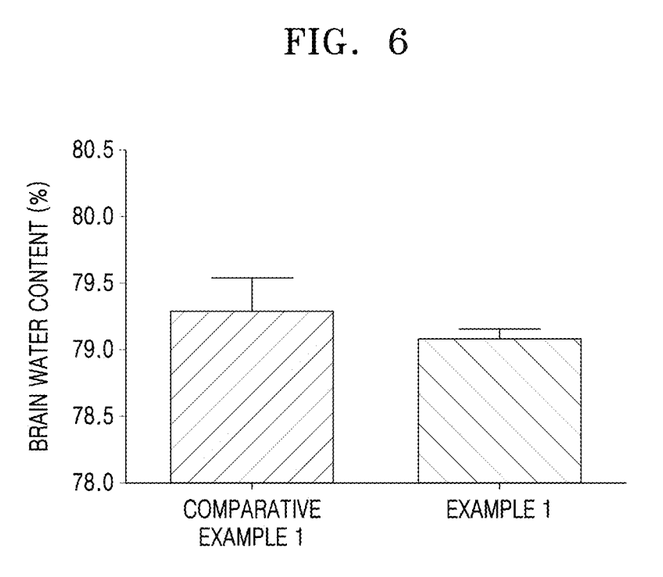

In addition, the brain water content in the left hemisphere is shown in FIG. 5, and the brain water content in the right hemisphere is shown in FIG. 6.

Referring to FIGS. 5 and 6, it was confirmed that the SD rat injected with the ceria nanocomposite according to Example 1 had a decreased brain water content, especially in the left hemisphere close to the left middle cerebral artery which is the SAH occurrence spot, compared to the control group (that is, the SD rat injected with PBS) of Comparative Example 1.

In Reference Example 1, 3 SD rats were tested, and in Example 1 and Comparative Example 1, 6 SD rats were respectively tested. The average value of each rat was indicated as a brain water content.

Evaluation Example 4: Effect of Ceria Nanocomposite on Reduction of Cell Death Rates in Terms of Therapeutic Effect on SAH To evaluate effect of the ceria nanocomposite prepared according to Example 1 on the reduction of cell death rates, the terminal deoxynucleotidyl transferase-mediated dUTP nick end-labeling (TUNEL) assay was performed. In detail, TUNEL was used, and the TUNEL assay is described in detail in the following research paper.

Methods in Molecular Biology, vol. 203: In Situ Detection of DNA Damage: Methods and Protocols Edited by: V. V. Didenko ©Humana Press Inc., Totowa, N.J.

Figure 7:
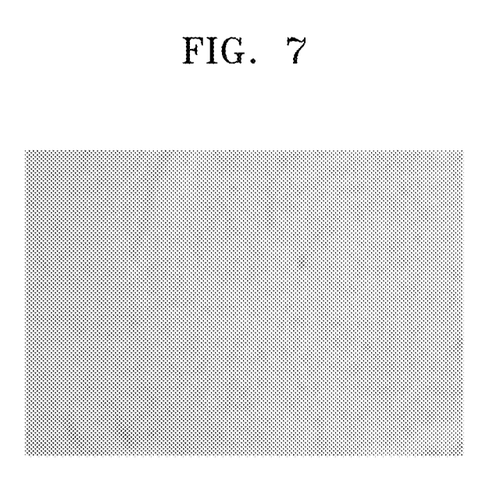
FIG. 7 is a photograph showing a cross-sectional view of the brain of a sprague dawley (SD) rat without subarachnoid hemorrhage.
Figure 8:
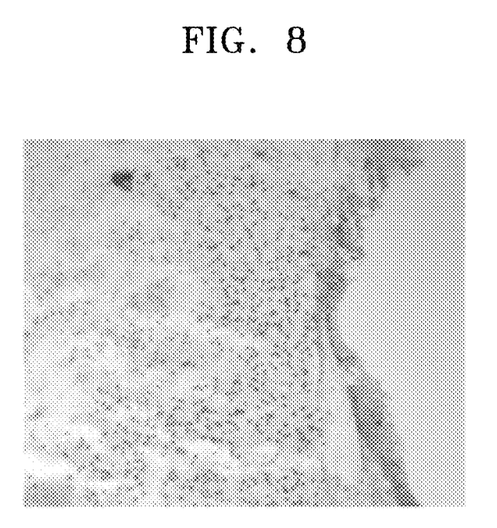
FIG. 8 is a photograph showing a cross-sectional view of the brain of an SD rat into which PBS is injected after subarachnoid hemorrhage occurs.

The brain was extracted from each of the SD rat (KOATECH Co., Ltd.) without SAH (sham model, Reference Example 1), the SD rat into which PBS (Amresco Company, pH 7.1 to 7.3) was injected twice in total, i.e., after 6 hours and 30 hours from the cause of SAH (Comparative Example 1), and the SD rat into which the ceria nanocomposite was injected twice in total, i.e., after 6 hours and 30 hours from the cause of SAH (Example 1). Then, the brain stem and the cerebellum were removed and cut into pieces. Photographs thereof were taken with an optical microscope, and the results are shown in FIGS. 7 and 8. Here, the experimental conditions from the start of the experiment to the brain extraction are the same as those of Evaluation Example 3 in Table 1.

Figure 9:
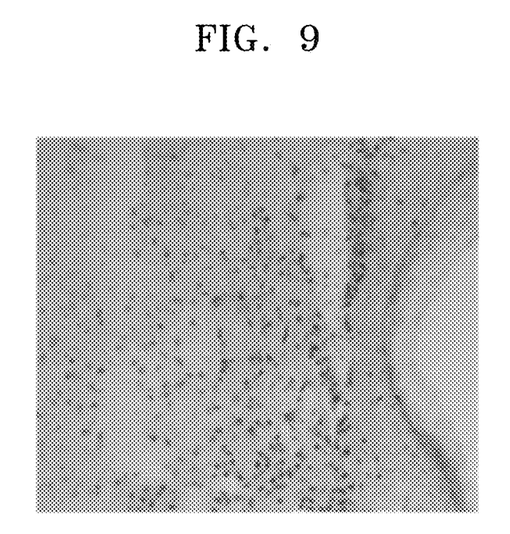
FIG. 9 is a photograph showing a cross-sectional view of the brain of an SD rat into which a ceria nanocomposite is injected after subarachnoid hemorrhage occurs.

FIG. 7 is a photograph showing a cross-sectional view of the brain of an SD rat without SAH (Reference Example 1), FIG. 8 is a photograph showing a cross-sectional view of the brain of an SD rat into which PBS was injected after SAH had occurred (Comparative Example 1), and FIG. 9 is a showing a cross-sectional view of the brain of an SD rat into which the ceria nanocomposite was injected after SAH had occurred (Example 1).

Referring to FIGS. 7 through 9, it was confirmed that the SD rat into which the ceria nanocomposite was injected according to Example 1 showed a decreased cell death rate compared to the control group (that is, the SD rat injected with PBS) of Comparative Example 1.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

The invention claimed is:

1. A ceria nanocomposite comprising a ceria nanoparticle and a surface modified layer disposed on a surface of the ceria nanoparticle,
   wherein the surface modified layer comprises a polyethylene glycol (PEG) residue,
   wherein the surface modified layer comprises an outer layer comprising the polyethylene glycol (PEG) residue and an inner layer whose one end is combined with the ceria nanoparticle and the other end is combined with the PEG residue,
   wherein the inner layer comprises a residue of a polyfunctional organic compound, and the residue of a polyfunctional organic compound has a first terminal residue combined with the ceria nanoparticle and a second terminal residue combined with the PEG residue of the outer layer,
   wherein the polyfunctional organic compound comprises an aliphatic amino carboxylic acid,
   wherein the PEG residue has a third terminal residue which is combined with the second terminal residue of the residue of a polyfunctional organic compound included in the inner layer,
   wherein the first terminal residue is a carboxylic group (—COOH), the second terminal residue is an amino group (—NH$_2$), and the third terminal residue is a succinimidyl group,
   wherein there is no other group combined with the polyethylene glycol residue of the outer layer except for the residue of the polyfunctional organic compound,
   wherein the PEG residue is a residue of methoxy PEG succinimidyl glutarate, methoxy PEG succinimidyl barate, methoxy PEG succinimidyl carbonate, methoxy PEG succinimidyl succinate, methoxy PEG succinimidyl propionate, or a combination thereof.

2. The ceria nanocomposite of claim 1, wherein the ceria nanocomposite has an average particle diameter of 5 nm to 100 nm.

3. A method of preparing the ceria nanocomposite of claim 1 for treating subarachnoid hemorrhage, the method comprising:
   preparing a mixed solution containing a cerium precursor, a polyfunctional dispersion stabilizer which comprises an aliphatic amino carboxylic acid, and a first solvent;
   heating the mixed solution to prepare a ceria nanoparticle in which the polyfunctional dispersion stabilizer is attached to a surface of the ceria nanoparticle; and
   mixing the ceria nanoparticle with a polyethylene glycol derivative in a second solvent such that the polyfunctional dispersion stabilizer and the polyethylene glycol derivative are combined together and the ceria nanocomposite is thereby prepared;
   wherein the PEG derivative comprises methoxy PEG succinimidyl glutarate, methoxy PEG succinimidyl barate, methoxy PEG succinimidyl carbonate, methoxy PEG succinimidyl succinate, methoxy PEG succinimidyl propionate, or a combination thereof.

4. The method of claim 3, wherein the first solvent and the second solvent are each an aqueous solvent.

5. The method of claim 3, wherein the cerium precursor comprises cerium(III) acetate hydrate, cerium(III) acetylacetonate hydrate, cerium(III) carbonate hydrate, cerium(IV) hydroxide, cerium(III) fluoride, cerium(IV) fluoride, cerium (III) chloride, cerium(III) chloride heptahydrate, cerium(III) bromide, cerium(III) iodide, cerium(III) nitrate hexahydrate, cerium(III) oxalate hydrate, cerium(III) sulfate, cerium(III) sulfate hydrate, cerium(IV) sulfate, or a combination thereof.

6. A pharmaceutical composition comprising the ceria nanocomposite of claim 1.

* * * * *